United States Patent [19]
Green

[11] Patent Number: 5,829,976
[45] Date of Patent: Nov. 3, 1998

[54] MEDICAMENT-CONTAINING INTERPROXIMAL DENTAL BRUSH

[76] Inventor: Warren F. Green, 10 Concord Rd., Wayland, Mass. 01778

[21] Appl. No.: 769,959

[22] Filed: Dec. 19, 1996

Related U.S. Application Data

[60] Provisional application No. 60/015,413, Apr. 12, 1996.

[51] Int. Cl. [6] ........................................... A61C 5/04
[52] U.S. Cl. ........................... 433/89; 401/134; 401/145; 401/269; 601/162
[58] Field of Search ........................ 433/80, 89; 401/134, 401/145, 152, 157, 269; 601/162, 165

[56] References Cited

U.S. PATENT DOCUMENTS

| | | | |
|---|---|---|---|
| 2,793,381 | 5/1957 | McWhorter | 401/145 |
| 3,391,696 | 7/1968 | Woodward | 433/89 |
| 3,480,009 | 11/1969 | Sinai | 601/462 |
| 3,910,706 | 10/1975 | Del Bon | 401/134 |
| 4,049,354 | 9/1977 | O'Rourke | 401/134 |
| 4,457,711 | 7/1984 | Maloney et al. | 433/80 |
| 4,640,637 | 2/1987 | Winthrop | 401/134 |
| 4,863,380 | 9/1989 | Creed | 433/89 |
| 5,098,297 | 3/1992 | Chari et al. | 433/80 |
| 5,152,742 | 10/1992 | Simpson | 401/134 |
| 5,283,924 | 2/1994 | Kaminski et al. | 15/244.1 |

*Primary Examiner*—John J. Wilson
*Attorney, Agent, or Firm*—Weingarten, Schurgin, Gagnebin & Hayes LLP

[57] ABSTRACT

A dental brush having a flexible fibrous tip with internal cannula to allow medicament, such as tetracycline, chlorhexidine or stannous fluoride, or combinations thereof to flow through the fibrous tip. The flexible fibrous tip includes a nonwoven tufted surface that completely covers the tip to remove plaque. The applicator tip fits between the teeth and the gum line and delivers both physical and chemical treatment to interproximal periodontal pockets. The medicament solution is stored in a disposable sealed and sterile cartridge and is held in the base of the device. A pump built into the base provides pressure to push the medicament through the cannula to the fibrous brush tip to provide site-specific dosage-controlled treatment. The brush tip is disposable and provides effective interproximal subgingival debridement and site-specific application of medication to infected areas.

11 Claims, 2 Drawing Sheets

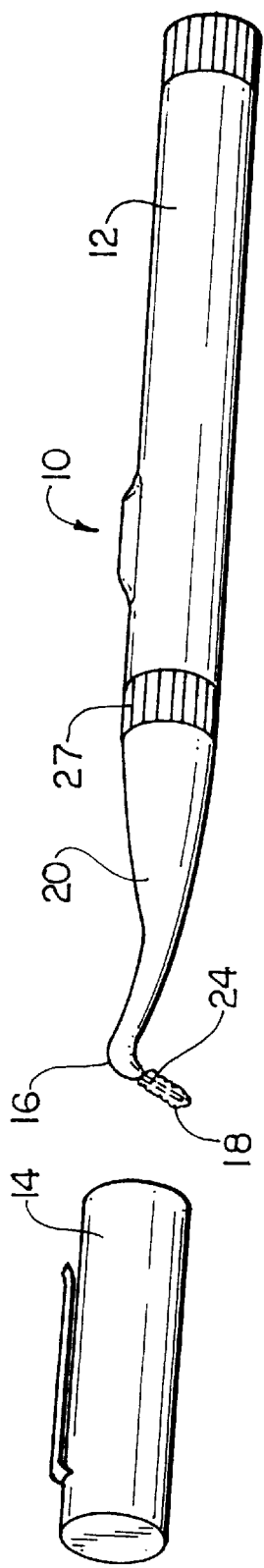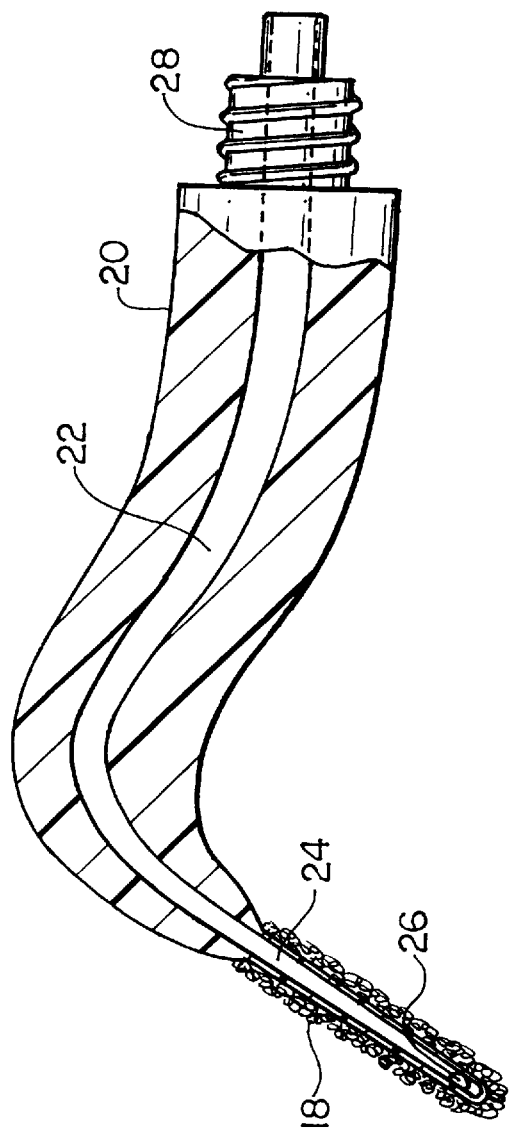
FIG. 1
FIG. 2

MEDICAMENT-CONTAINING INTERPROXIMAL DENTAL BRUSH

CROSS-REFERENCE TO RELATED APPLICATIONS

This application is based on Provisional Application Ser. No. 60/015,413 filed Apr. 12, 1996.

FIELD OF THE INVENTION

This invention relates to dental instruments, and more particularly to a dental instrument that includes a fibrous interproximal brush tip which provides medication and debridement treatments to infected areas of teeth and gums.

BACKGROUND OF THE INVENTION

Plaque is an uncalcified mucoprotein material which acts as a growing medium for bacteria. Many types of bacteria and the plaque in which they grow are the cause of tooth decay and periodontal disease affecting approximately 90% of the adult population. To reduce the incidence of periodontal disease, it is generally recommended that plaque be removed at least once a day. Common methods for removing plaque include toothbrushing, flossing, and mouthwash. Regular toothbrushing, even with the various available electric devices, cleans approximately 80% of the total exposed tooth surface. The remaining 20% interproximally are in the area where the most severe and involved periodontal disease occurs. Mouthwash is a means for delivering medicaments to diseased areas. However, mouthwashes suffer from an inability to penetrate significantly below the gum line, and therefore may not contact the diseased areas. While many devices have been manufactured to clean teeth, including rotary and sonic toothbrushes, none are capable of penetrating well into the periodontal pocket.

A considerable body of evidence shows that debridement, i.e., removal of calculus and plaque from the surface of the tooth, in the infected areas is not enough to effectively remove the cause of periodontal disease. The real issue in effective treatment in periodontal disease is detoxification and removal of bacterial endotoxins on the tooth root surface. Moreover, as the periodontal pocket deepens (exposing more root surface) the efficacy of penetrating and treating the area diminishes significantly.

U.S. Pat. No. 5,283,924 to Kaminski et al. discloses a dental instrument including a foam coated tip for use in oral hygiene. However, foam does not have the capability to remove plaque from deep within the periodontal pocket.

SUMMARY OF THE INVENTION

The invention is a disposable fibrous dental applicator tip that is fed medicament via a cannula from the body or base of the instrument. The tip of the invention includes a flexible cannula core which is completely covered with a nonwoven, tufted surface which is capable of removing plaque. The fibrous applicator tip is specifically designed to massage the interproximal root surfaces and simultaneously deliver medication directed at the sources of periodontal diseases, such as bacteria and endotoxins in the gingival sulcus between the teeth. The various medicaments are dispensed through a hole or holes located in a flexible probe in the cannula to chemically detoxify the affected areas. The types of medicaments which could be applied include antimicrobials, anti-inflammatories, surfactants, sealants, and other therapeutic medicaments which may be available by prescription or over-the-counter. Exemplary medicaments include tetracycline, chlorhexidine and stannous fluoride. The combination of agitation by the fibrous applicator tip along with application of medicaments directly to the affected area permits effective, site-specific treatment of periodontal diseases. The medicaments used in conjunction with the device are contained in sealed sterile disposable cartridges. A pump built into the base provides pressure to force the medicament through the tip for application directly to the affected area.

The site-specific applicator tip of the invention affords the user more control over the application of the medicament, particularly when prescription medicaments are used. The additional control afforded by the applicator tip of the invention also permits the dentist to better prescribe and control both dosage and dosage frequency, as well as duration of the treatment. Although designed primarily for home use, a doctor or dentist may prescribe various medications and dosages for specific needs and effectiveness of treatment.

The design of the tip for penetration and scrub as well as the delivery of medication makes the device highly effective in removing plaque and neutralizing endotoxins and collagenases found in the periodontal pocket. As used herein, the term "scrub" refers to mechanical removal of plaque. In addition, the choice and dosage of medication is virtually limitless. Drugs now available and future drugs could be adapted for use with the present invention.

BRIEF DESCRIPTION OF THE DRAWINGS

The invention will be more fully understood from the following detailed description taken in conjunction with the accompanying drawings in which:

FIG. 1 is an external side view of an embodiment of the invention;

FIG. 2 is cross-sectional view of the applicator tip of the invention;

DETAILED DESCRIPTION OF THE INVENTION

Figure 3:
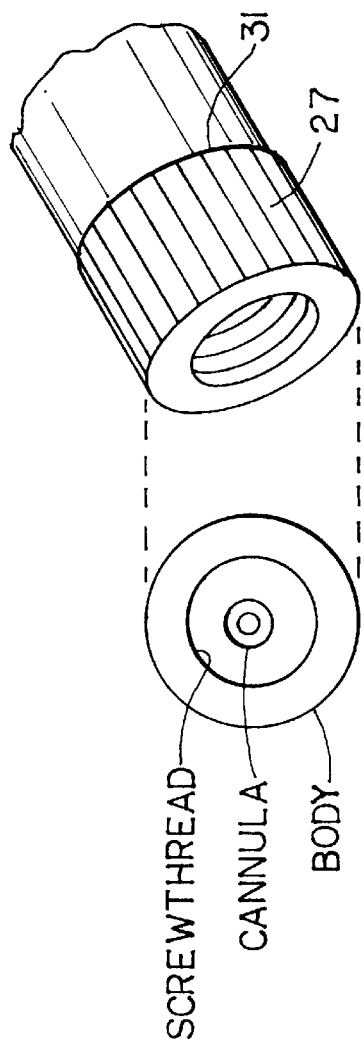
FIG. 3 is a perspective view of the swivel connection of the invention.

FIG. 1 shows an external view of an embodiment of the invention. The device 10 includes an applicator base 12, a curved tip 20, and a swivel connection 27 connecting the tip 20 to the applicator base 12. A snap-on cover cap 14 may also be included to cover the tip 20. The applicator base 12 may assume any shape, however the ends are preferably cylindrical. There may be indented or flattened areas on the applicator base 12 to facilitate grip by the user.

The tip 20 comprises an angled section 16 and an exposed flexible probe 24. Nonwoven tufted scrub material 18, comprised of materials such as nylon, polyurethane foams or polyolefins is attached to the flexible probe 24 by an suitable adhesive, or other bonding or manufacturing method known in the art. Alternatively, the material may be comanufactured during the fabrication of the tip. The material is preferably a nonwoven tufted material that completely surrounds the probe 24. In contrast to brush bristles, several features of the scrub material 18 make it suitable for use in the invention. Preferably, the scrub material 18 is rugged enough to scrub away plaque on the root surface of a tooth, dense enough to protect the cannula core, and soft enough to be non-irritating to gingival tissue, yet porous to allow medicament to flow through it. The scrub material 18 may be of any stiffness or length appropriate for the particular application. In one embodiment, the scrub material has a nap in the range of 0.25 to 1.0 mm. As shown in FIG. 1, the angled section 16 of the applicator tip is bent at approximately 70°. However, other angles are possible to configure the invention to suit the needs of individual patients. The cover cap 14 fits over the applicator tip 20 and protects the tip from damage when the device is not in use.

FIG. 2 shows an enlarged cross-sectional view of the applicator tip 20 of the invention. The applicator tip 20 is preferably manufactured as a single piece of plastic, plastic over metal, or other material to provide a lightweight, durable instrument that is easy to control by the user. The applicator tip 20 is preferably a disposable, screw-on tip with a cannula 22, and a flexible probe 24 covered with a nonwoven tufted scrub material 18 at one end. In one embodiment, a screw connection 28 at the opposite end can permit the applicator tip to be attached to the base. Other connection means may also be used.

The cannula 22 directs medicaments to flow from a medicament reservoir to a flexible portion 24 of the applicator tip 20 that is covered with nonwoven tufted scrub material 18. Medicament contained in the reservoir flows through the flexible probe 24 and exits through one or more holes 26 to saturate the scrub fibers 18. For clarity, a single hole is shown in FIG. 2. The size and flexible nature of the flexible probe 24 permits insertion of the fibers into tight recesses between teeth or between the gum line and the tooth. Accordingly, the applicator tip 20, cannula core 24, and scrub fibers 18 may be made in any size that is appropriate for implementation into a particular dental application. For example, if a patient has larger gaps between teeth, or the interproximal periodontal pocket is deeper than normal, a larger tip will be more useful for optimal interproximal penetration. In one embodiment, the cannula core 24 is 4 mm in length, 1.5 mm in diameter at the proximal end and 1 mm in diameter at the distal end. Preferably, the entire length of the flexible probe 24 is covered with the scrub fibers 18. Moreover, the cannula core may take a variety of shapes, such as oval, curved, etc., in order to provide optimum debridement.

During use, the scrub fibers 18 become saturated with medicament, and as the tooth is scrubbed, the medicament is simultaneously applied to the neck of the tooth and below the gum line. Thus, the tip 20 of the invention can penetrate into periodontal pocket areas to provide concurrent plaque debridement and medication. Although an approximate 70° angle is shown in FIG. 2, it is possible that tips with a variety of angles could be manufactured and used on the same base to facilitate access to hard-to-reach areas.

FIG. 3 shows a swivel connection 27 that may be included on the applicator tip 20 to allow easy, accurate, and secure assembly of the screw connection 28 onto the applicator base 12. The swivel is preferably internally threaded to facilitate attachment of the tip 20 on the screw connection 28, the cannula 22 extends beyond the lower edge 31 of the screw connection 28 to provide fluid communication between the fluid reservoir and the cannula tip as described hereinbelow.

Figure 4:
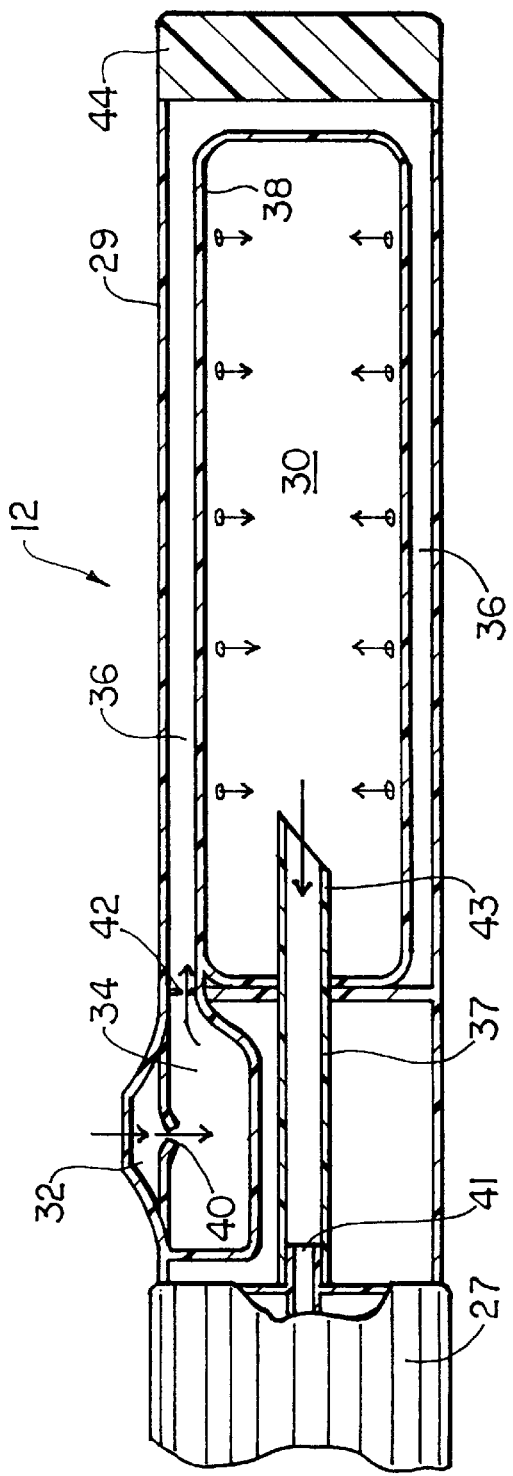
FIG. 4 is a cross-sectional view of the base portion of the invention.

FIG. 4 shows a cross-sectional view of the base of the instrument. The applicator base 12 includes an airtight, rigid casing 29 that is capable of holding a medicament reservoir 30. The swivel connection 27 attaches to the applicator base 12 at one end, and the end of the cannula 41 mates with an extension cannula 37. In one embodiment, the cannula 41 and the extension cannula 37 are connected by a friction grip. The extension cannula 37 fits over the end of the cannula 41 and extends into the interior of the medicament reservoir 30, terminating in a sharp end 43 that is capable of piercing the medicament reservoir. The opposite end of the base includes an end hub 44 that may be opened to replace the reservoir cartridges and seal the cartridges in the chamber.

A finger pump 32 is incorporated into the applicator base 12 to allow the user to apply pressure from any compressible fluid to the reservoir and force the medicament from the reservoir into the tip of the instrument. In one embodiment, finger pump 32 pressurizes air in an air bladder 34 and the compressed air is forced into the space 36 between the casing 29 and the reservoir wall 38. One-way valves 40 and 42 maintain the air pressure generated by the finger pump 32 so that the reservoir wall gradually collapses and forces the medicament through the cannula and into the tip of the instrument. Preferably, the medicament reservoir 30 is made from a soft, collapsible, disposable material such as light, clear polyethylene, polypropylene, or other suitable material known in the art. Preferably, the reservoir has more thickness at the puncture end to maintain a seal between the extension cannula 37 and the reservoir when in use. The puncture end may be colored and is preferably 2–3 mm in thickness. The other sides of the reservoir are of the appropriate thickness to permit the reservoir to collapse when air pressure is generated in the base.

The replaceable nature of the reservoir allows the user to select a variety of medications for therapeutic application. To replace the medicament reservoir 30, the user opens the end hub 44 and extracts the empty reservoir cartridge. The new reservoir cartridge with the appropriate medicament is inserted into the applicator base 12 and the end of the reservoir is punctured by the sharp end 43 of the extension cannula 37. A seal forms between the extension cannula 37 and the wall of the reservoir, and the end hub 44 is replaced. Actuation of the finger pump 32 repressurizes the instrument to allow new medicament to flow. Alternatively, the cannula may be constructed of a single piece of material, and include a polycarbonate needle or a trocar. Additionally, a one-way valve may be used.

Medicaments useful with the present invention include, but are not limited to, keratinizing agents, topical anesthetic or desensitizing agents, antimicrobial agents, antiviral agents, surfactants, sealants, chlorhexidine, antibiotics, stannous fluoride, or other medicament that is capable of moving through the instrument. Preferably, such medicaments are in liquid or nonviscous gel form, soluble in water, and do not precipitate in suspension.

Although the invention has been shown and described with respect to an illustrative embodiment thereof, it should be appreciated that the foregoing and various other changes, omissions, and additions in the form and detail thereof may be made without departing from the spirit and scope of the invention as delineated in the claims.

I claim:

1. An interproximal dental brush, comprising:
    a tip portion comprising
        a tip body having a first end and a second end and a cannula disposed in said body from said first end to said second end;
        a hollow, flexible probe attached to said first end of said tip body and in fluid communication with said cannula, said flexible probe having at least one orifice; and scrub fibers attached to said flexible probe;

a swivel connection attached to said second end of said tip portion, said swivel connection in fluid communication with said cannula; and a base body attached to said swivel connection and comprising a pump; and a medicament reservoir in fluid communication with said swivel connection, wherein said pump provides pressure to walls of said medicament reservoir to move medicament to said flexible probe.

2. The interproximal dental brush of claim 1 wherein said scrub fibers comprise nonwoven tufted material capable of removing plaque.

3. The interproximal dental brush of claim 1 wherein said scrub fibers have a nap in the range of approximately 0.25 millimeters to approximately 1.0 millimeters.

4. The interproximal dental brush of claim 1 wherein said scrub fibers comprise nylon or polyurethane foams.

5. The interproximal dental brush of claim 1 wherein said scrub fibers comprise polyolefins.

6. The interproximal dental brush of claim 1 further comprising a cap, said cap sized to cover said tip portion.

7. The interproximal dental brush of claim 1 wherein said base includes a grip portion.

8. The interproximal dental brush of claim 1 wherein said medicament reservoir comprises a disposable cartridge.

9. The interproximal dental brush of claim 1 wherein said cannula includes a needle or trocar for puncturing said medicament reservoir.

10. The interproximal dental brush of claim 1 wherein said pump further comprises an air bladder for forcing the medicament forward to the tip.

11. The interproximal dental brush of claim 1 wherein the medicament is selected from the group consisting of anti-microbial agents, anti-inflammatories, surfactants, sealants, keratinizing agents, topical anesthetics, anti-viral agents, chlorhexidine, antibiotics, tetracycline, stannous flouride and other therapeutic agents.

* * * * *